United States Patent [19]

Teo

[11] Patent Number: 5,911,221
[45] Date of Patent: Jun. 15, 1999

[54] STATIC SCANHEAD SWITCHING ALONG ELEVATION FOR FORMING ULTRASOUND BEAM LINE

[75] Inventor: Tat-Jin Teo, Redmond, Wash.

[73] Assignee: Siemens Medical Systems Inc., Iselin, N.J.

[21] Appl. No.: 08/671,323

[22] Filed: Jun. 25, 1996

[51] Int. Cl.⁶ .................................................. A61B 8/00
[52] U.S. Cl. ................................................... 128/661.01
[58] Field of Search ........................ 128/660.08, 661.01, 128/660.07; 73/625, 626, 628

[56] References Cited

U.S. PATENT DOCUMENTS

| | | |
|---|---|---|
| 4,180,790 | 12/1979 | Thomas . |
| 5,349,262 | 9/1994 | Grenon et al. . |
| 5,490,512 | 2/1996 | Kwon et al. ........................ 128/661.01 |

OTHER PUBLICATIONS

Defranould et al.; "Design of a Two Dimensional Array for B and C Ultrasonic Imaging System;" 1977 Ultrasonics Symposium Proceedings, IEEE Cat. 77CH1264–1SU.

Lockwood et al.; "Optimizing Sparse Two–Dimensional Transducer Arrays Using an Effective Aperture Approach;" Date Unknown.

*Primary Examiner*—George Manuel

[57] ABSTRACT

A static switching scheme along transducer elevation for obtaining beam line from multiple firings. Between firings for an associated beam line the elevation aperture is changed depending upon the image plane focus depth. For a single image plane focus beyond a deepest break point, a widest elevation aperture is used during one firing. During other firings for the beam line the elevation aperture is narrowed. Each of multiple break points separate a distinct depth region. Echo data for a beam line includes echo data from one firing for one region and from another firing for another region. Echo data from multiple firings is blended in vicinity of region boundaries. For multiple image plane foci applications, the elevation aperture for a given firing is determined by the target image plane focus for such firing.

22 Claims, 7 Drawing Sheets

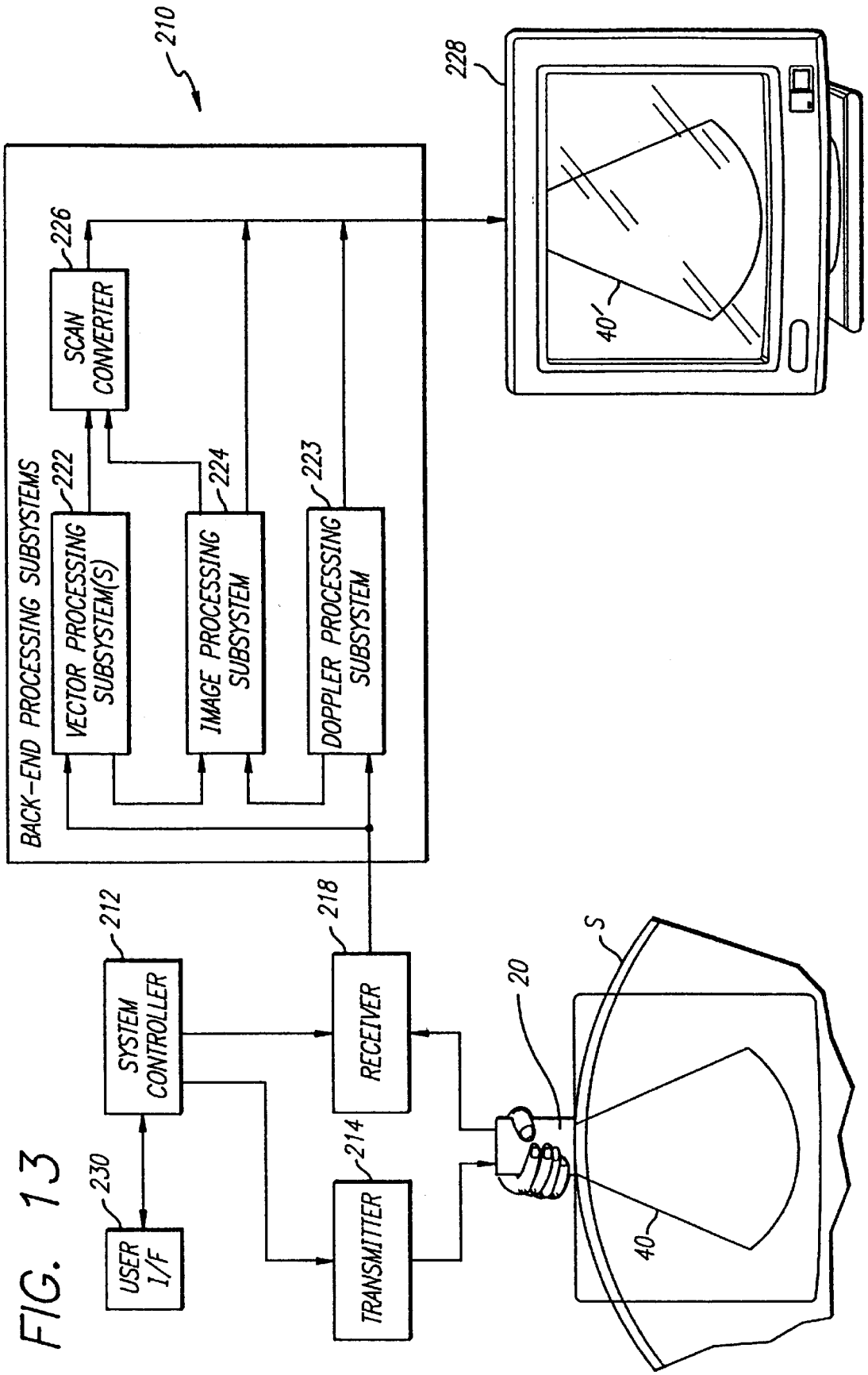

STATIC SCANHEAD SWITCHING ALONG ELEVATION FOR FORMING ULTRASOUND BEAM LINE

BACKGROUND OF THE INVENTION

This invention relates to medical, diagnostic ultrasound transducer array configurations and switching schemes, and more particularly to a switching system and method for forming ultrasound beam lines.

Medical diagnostic ultrasound systems are commonly used to generate two-dimensional diagnostic images of internal features within a patient's body. To do so, a sonographer positions an ultrasound transducer probe adjacent to a patient's target area. The probe is a non-intrusive device including an array of acoustic transducer elements. The transducer elements emit ultrasonic energy at a frequency on the order of 2.0 MHz to 10 MHz. The transmitted ultrasound energy propagates into the patient where it is in part absorbed, dispersed, refracted, and reflected by internal structures. Reflected ultrasound energy is received back at the transducer probe where it is converted back into electronic signals. Body tissues, for example, appear as discontinuities or impedance changes in the converted electronic signals.

Converted electronic signal samples undergo beamforming to correlate the samples in time and space to a patient's target area. Exemplary beamforming parameters for controlling the imaging process include focus, steering, apodization and aperture. Focus is a time delay profile of active transducer elements. Steering is the control of focus depth points along azimuth and/or elevation axes of a transducer probe scan. Apodization is a voltage weighting profile of active transducer elements. Aperture is the control of the number of transducer elements which are active along azimuth or elevation axes of the transducer probe for a given scan. Beamformed data is processed to analyze echo, doppler, and flow information and obtain a cross-sectional image of the patient's targeted anatomy (e.g., tissue, flow, doppler).

A conventional image is a brightness image (i.e., referred to as a 'B-mode image') in which component pixels are brightened in proportion to a corresponding echo sample strength. The B-mode image represents a cross section of the patient target area through a transducer's scanning plane (e.g., xz-plane). Typically the B-mode image is a gray scale image in which the range of lighter to darker gray-scale shades correspond to decreasing brightness or echo strength. The typical ultrasound B-mode image is formed by a linear scan or sector scan of the patient's target area by the transducer probe.

Among known transducer array configurations are linear 1-dimensional ('1-D') arrays and non-linear multi-dimensional arrays. A 1-D array includes a single row of transducer elements. A multi-dimensional array includes multiple rows of transducer elements along at least a portion of the array. A linear array having 64 transducer elements has 64 channels to control. A multi-dimensional array having n rows of 64 elements per row has as many as 64×n channels to control.

FIG. 1 depicts a conventional filled 2-D ultrasound transducer array 10. The array 10 includes a plurality of rows 12. Each row 12 includes a plurality of transducer elements 14. Each element 14 is formed of a piezoelectric material. The rows 12 extend along an azimuthal ("x") direction in parallel with one another. The rows 12 are spaced in an orthogonal elevation ("y") direction. For the conventional 2-D array each element 14 is independently controlled to perform either one or both of transmitting and receiving ultrasound signals. For a 2-D array 10 having 5 rows 12 and 64 transducer elements 14 per row, there are 64×5 channels to control. The transducer 10 emits and receives ultrasound signals to define an xz image plane 16.

FIG. 2 depicts a conventional 1.5-D ultrasound transducer array 20. The array 20 includes a plurality of rows 22 of transducer elements 24. Each row 22 extends along an azimuthal ("x") direction. The rows 22 are parallel and spaced orthogonally in an elevation ("y") direction. In contrast to the 2-D array, however, the transducer elements 24 are not independently controlled. For a conventional 1.5-D array an element 24a in one row 22-B1 is coupled to a corresponding element 24a in a symmetrical row 22-B2. A center row 22-A defines an axis of symmetry. Corresponding elements in the first row on each side of the center row (i.e., 22-B1 and 22-B2) are electronically connected. Similarly, corresponding elements in the second row, if any, on each side of the center row (i.e., 22-C1 and 22-C2) are electronically connected. Thus, elements 24a of rows 22-B1 and 22-B2 are connected, elements 24b of rows 22-B1 and 22-B2 are separately connected, elements 24a of rows 22-C1 and 22-C2 are separately connected, and elements 24b of rows 22-C1 and 22-C2 are separately connected. For a 1.5-D array 20 having five rows, 22-A, 22-B1, 22-B2, 22-C1 and 22-C2, in which each row has 64 elements, there are 64×3 separate channels to control. The transducer 20 emits and receives ultrasound signals to define an xz image plane 26.

To develop an image of a scanned image plane of a patient, the transducer elements are controlled to define aperture, focus, steering and apodization profiles. For a 1.5-D array beamforming controls along the elevation (y-axis) are limited. Specifically, steering of the beam is controlled along the azimuth, but not the elevation. Focus along the elevation is symmetrical. Apodization profiles along the elevation are symmetrical. This invention is directed toward a switching scheme for a static scanhead 1.5-D transducer array which improves image resolution of a displayed image plane.

SUMMARY OF THE INVENTION

According to the invention, a static scanhead switching scheme is implemented along the elevation of the transducer to obtain a beam line from multiple firings of a transducer array. A transducer field of view encompasses multiple beam lines. For each scanning cycle received echo data corresponding to each beam line within the field of view is used to generate a frame of image data. The array is fired and echo data is received without dynamically changing elevation beamforming parameters. By static scanhead switching along the elevation it is meant that the elevation beamforming parameters may vary from one firing/receive period to another, but remain the same during a given firing/receive period.

Beam line as used herein refers to the image plane and elevation slice of the beam pattern formed by the firing and returning ultrasound energy. Received ultrasound energy is converted into electrical signals from which echo data is derived. There is echo data associated with each beam line. According to the invention multiple firing/receive periods are performed to obtain the echo data for a given beam line. The elevation aperture is varied for the firings. By changing the elevation aperture elevation slice of the beam pattern changes. Echo data in the vicinity of the elevation focus is used for the beam line while other echo data is disregarded.

Over multiple firings, regions of echo data are captured to form an entire beam line.

According to one aspect of the invention, for applications with a single image plane focus per beam line the number of firings per beam line and the elevation aperture size per firing depend on the depth of the image plane focus and a defined number of break point depths. The number of break points is defined according to the potential elevation aperture permutations. A 1.5-D array having 5 rows, for example, has three elevation aperture size permutations. For an image plane focus at a shallow depth less than a first break point depth, a single firing having a narrow first elevation aperture size is used. For an image plane focus at a depth between a first break point and a second breakpoint, two firings are performed. During one firing the first elevation aperture size is used to capture echo data within a first region where depth is less than the first break point. During a second firing a second elevation aperture size wider than the first aperture size is used to capture echo data within a second region between the first and second break point depths. For an image plane focus at a depth deeper than the second breakpoint, three firings are performed. During one firing the first elevation aperture size is used to capture echo data within a first region where depth is less than the first break point. During a second firing, the second elevation aperture size is used to capture echo data within a second region between the first and second break point depths. During a third firing, a third elevation aperture size wider than the second elevation aperture size is used to capture echo data within a third region beyond the second break point depth. Echo data in the second and third regions is disregarded for the first firing. Echo data in the first and third regions is disregarded for the second firing. Echo data in the first and second regions is disregarded for the third firing.

According to another aspect of the invention, for applications using multiple image plane foci per beam line there are at least as many firings per beam line as there are image plane foci per beam line. The elevation aperture size for a given firing depends on the image plane focus for such firing and the number and depth of a breakpoint depth. For a firing in which the image plane focus is shallower than a first break point depth, a narrow first elevation aperture size is used. For a firing in which the image plane focus is between the first and a deeper second break point depth, a wider second elevation aperture size is used. For a firing in which the image plane focus is beyond the second break point depth, a yet wider third elevation aperture size is used. For 1.5-D array with three elevation aperture permutations there are three regions and two break points separating the regions. Echo data in a first region shallower than the first break point depth is captured for firings using the narrow first aperture size. Echo data in a second region between the two break points is captured for firings using the wider second aperture size. Echo data in a third region deeper than the second break point depth is captured for firings using the yet wider third aperture size. Echo data in the second and third regions are disregarded for the firings using the first aperture size. Echo data in the first and third regions are disregarded for the firings using the second aperture size. Echo data in the first and second regions are disregarded for the firings using the third aperture size.

According to a preferred embodiment a beam line within a field of view of an ultrasound 1.5-D transducer array for a given scanning cycle is generated by defining a break point depth. For an image plane focus shallower than the break point depth, the beam line for the given scanning cycle is generated by firing the transducer array once, wherein elevation aperture is of a first size for the firing. For an image plane focus deeper than the break point depth, multiple firings of the transducer array are performed to generate the beam line for the given scanning cycle. Elevation aperture is of a first size during one of the multiple firings and is of a second size during another of the multiple firings. The second size is greater than the first size. The elevation aperture includes at least one row of transducer elements within the 1.5-D array for the first size and at least three rows of transducer elements within the 1.5-D array for the second size.

A first region includes depth shallower than the break point. At least one other region includes a depth deeper than the break point. Echo data associated with the beam line for the given scan cycle includes echo data within the first region for the one firing. Echo data outside the first region is disregarded for the one firing and echo data within the first region is disregarded for the another firing.

In one embodiment the break point depth is a first break point depth and a second break point depth also is defined. For an image plane focus between the first break point depth and second break point depth, two firings of the transducer array are performed to generate the beam line. Elevation aperture is of the first size during one of the two firings and is of the second size during the other of the two firings. The second size is greater than the first size. For an image plane focus deeper than the second break point depth, three firings of the transducer array are performed to generate the beam line. Elevation aperture is of the first size during one of the three firings, is of the second size during another of the three firings, and is of a third size during yet another of the three firings. The third size is greater than the second size and the second size is greater than the first size.

A first region includes a depth shallower than the first break point. A second region includes a depth between the first and second break point. A third region includes a depth deeper than the third break point. Echo data associated with the beam line for the given scan cycle includes (i) echo data within the first region for said one firing, (ii) echo data within the second region for said another firing, and (iii) echo data within the third region for said yet another firing. Echo data within the second region and third region is disregarded for said one firing. Echo data within the first region and third region is disregarded for said another firing. Echo data within the first region and second region is disregarded for said yet another firing.

According to another preferred embodiment a beam line having multiple image plane foci within a field of view of an ultrasound 1.5-D transducer array for a given scanning cycle is generated by defining a break point depth. A number of firings of the transducer array are performed for each beam line generated for a given scanning cycle. There is at least one firing per image plane focus along the beam line. Each firing has an image plane focus at only one of the multiple image plane foci. For each firing associated with the beam line being generated for the given scanning cycle, elevation aperture is set to a first aperture size for image plane focus which is shallower than the break point depth. Elevation aperture size is set to another aperture size, greater than the first aperture size, for image plane focus which is deeper than the break point depth. Transmit and receive beamforming parameters along the elevation are static for a given firing and a corresponding receive time period responsive to such given firing. A first region includes depth shallower than the break point. At least one other region includes depth deeper than the break point. Echo data associated with the beam line for the given scan cycle includes echo data within the first region for each firing in which elevation aperture is set to the first aperture size. Echo data outside the first region is disregarded for said each firing in which elevation aperture is set to the first aperture size. Echo data within the first region is disregarded for said each firing in which elevation aperture is set to another aperture size.

According to one advantage of the invention, beam line resolution is enhanced for a static 1.5-D ultrasound scanhead. According to another advantage of the invention, there is no reduction in frame rate for multiple foci applications in which the number of foci is at least the same as the number of elevation aperture permutations.

BRIEF DESCRIPTION OF THE DRAWINGS

FIG. 13 is a block diagram of a host medical diagnostic ultrasound system.

DESCRIPTION OF SPECIFIC EMBODIMENTS

Overview

Figure 1:
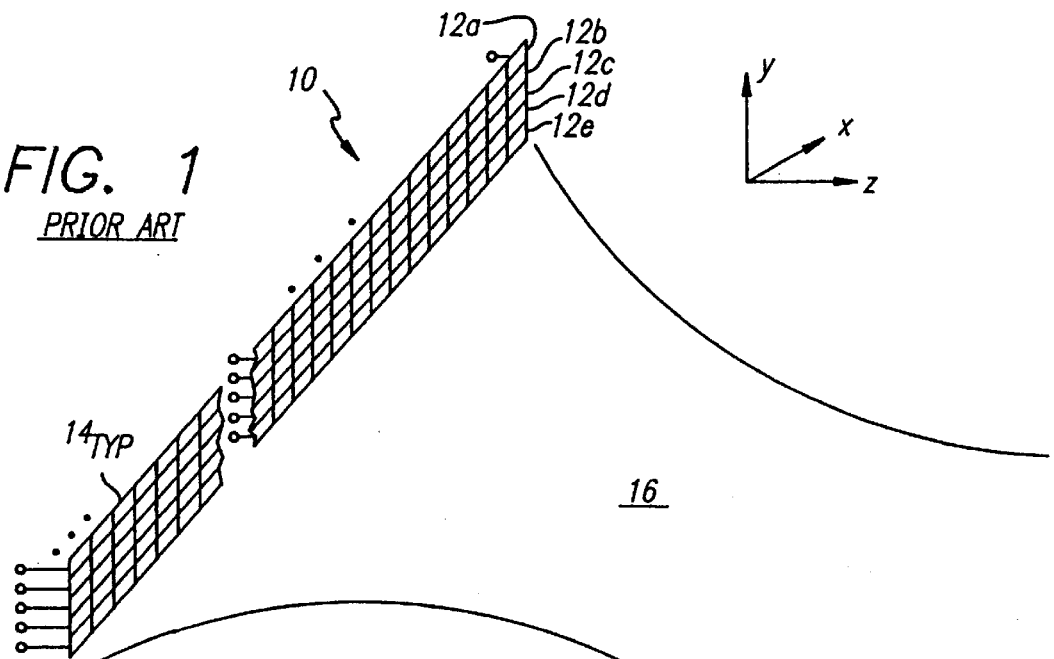
FIG. 1 is a diagram of a conventional 2-D ultrasound transducer array.
Figure 2:
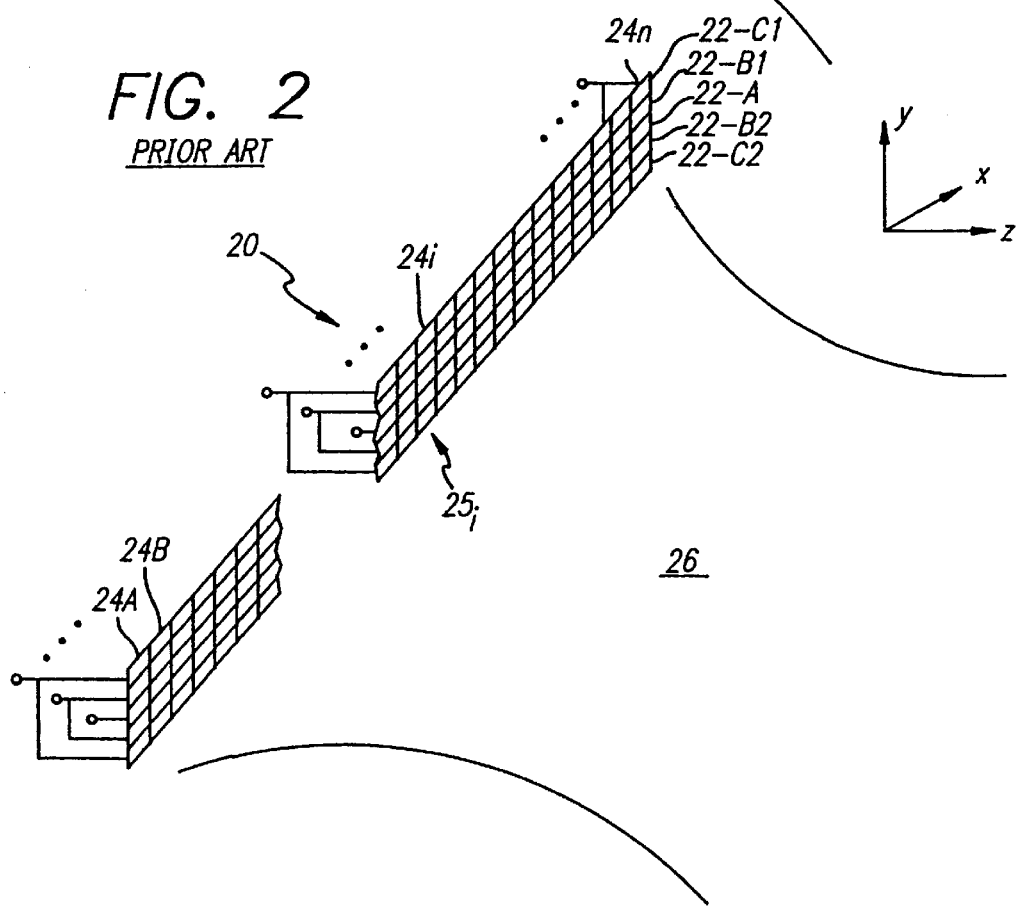
FIG. 2 is a diagram of a conventional 1.5-D ultrasound transducer array.
Figure 3:
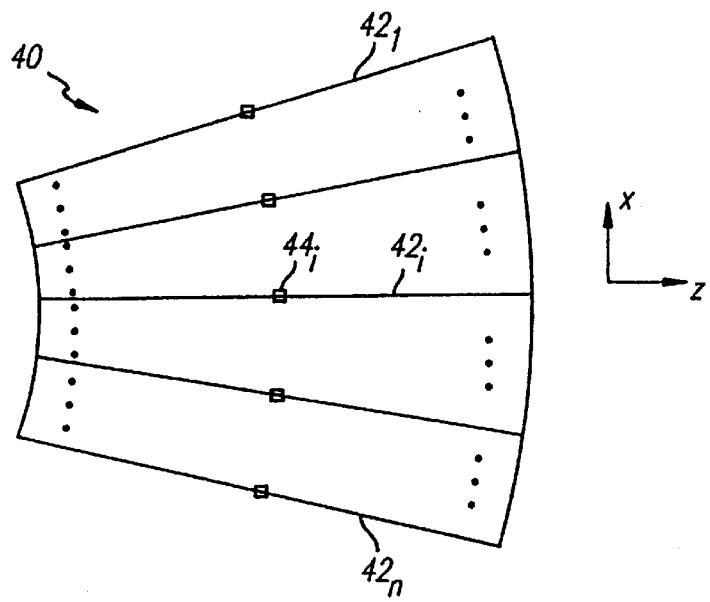
FIG. 3 is a diagram of a 1.5-D ultrasound transducer field of view formed by multiple beam lines.

FIG. 3 shows a diagram of a 1.5-D ultrasound transducer field of view 40. The field of view 40 corresponds to a display image area 40' (see FIG. 12). The field of view 40 is formed by beam data from a plurality of ultrasound beam lines 42. For a typical medical diagnostic application there are multiple beam lines $42_1$ through $42_n$. Exemplary numbers of beam lines for a 5×64 1.5-D transducer array 20 are 256 and 512. The number of beam lines 42 encompassing the array field of view 40, however, may vary. Each beam line $42_i$ corresponds to a transmitted beam having a given focus $44_i$. Echo data received at the array 20 is processed to obtain image data corresponding to such beam line. Typically, echo data from multiple beam lines is used to correlate a gray scale value for a given point within the field of view 40. Echo processing, doppler processing, scan conversion processing, image processing and video processing are performed on received data to obtain a final displayed image encompassing the field of view 40.

According to one aspect of the invention each beam line 42 is derived from one or more array 20 firings. A firing corresponds to a single transmit timing and voltage weighting pattern of beamforming parameters applied to the elements 24 across the array 20. Because the array 20 is a 1.5-D array, there is no steering along the elevation. In addition, focus and apodization are symmetrical along the elevation. Such limitation results from electrically coupling corresponding elements of symmetrical rows 22. For a 5 row embodiment the center element of a column is controlled. The next outer element on each side of the center element are controlled in common. The most outer element on each side of the center element also are controlled in common. Thus, three independent channels are controlled per column.

Figure 4:
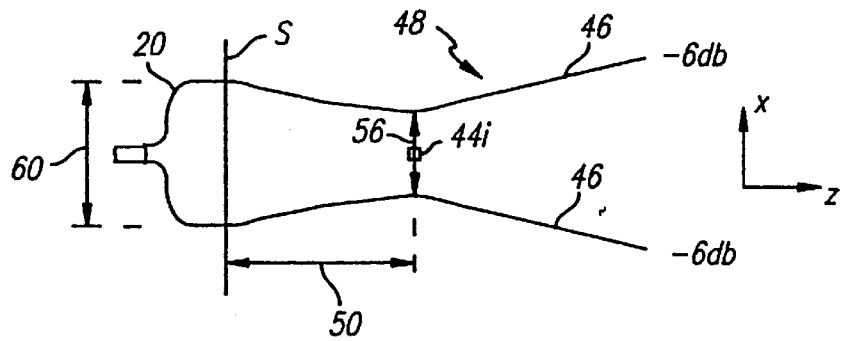
FIG. 4 is a diagram of an xz image plane for a given beam line of FIG. 3.
Figure 5:
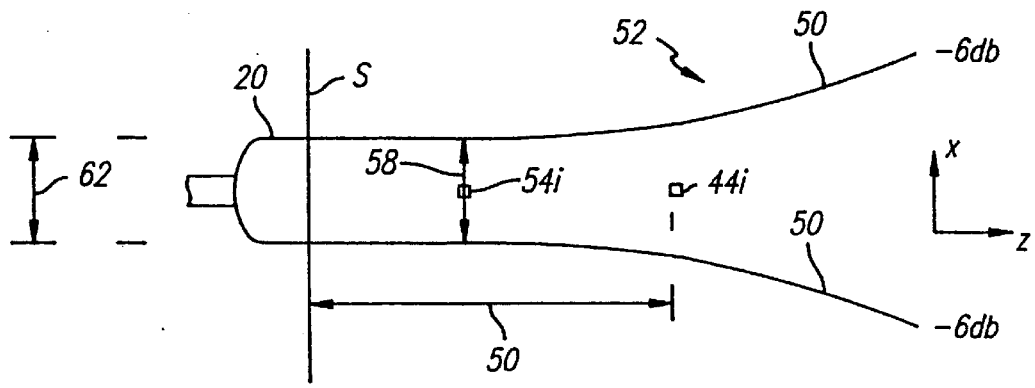
FIG. 5 is a diagram of a yz elevation slice for a given beam line of FIG. 3.

FIGS. 4 and 5 show beam profiles for a given beam line $42_i$. FIG. 4 shows −6 dB lines 46 for an xz image plane 48 having a focus $44_i$ at depth 50 below the skin S. FIG. 5 shows −6 dB lines 51 for a yz elevation slice 52 having an elevation focus $54_i$. The image plane focus $44_i$ at depth 50 also is shown on FIG. 5 for purposes of comparison. The −6 dB width of the image plane 48 is shown at line 56. The −6 dB elevation slice thickness is shown at line 58. Such beam profiles 46, 48 correspond to an azimuthal aperture size 60 and an elevation aperture size 62. The beam profiles 46, 48 correspond to a single firing of array 20. The illustrative lines of the beam profiles shown in each of FIGS. 6, 7, 8, 9, 11 and 12, although not specifically labelled, also are shown by their −6 dB lines. The −6 dB lines are used as a matter of convenience. Other lines such as −20 dB lines could be used to characterize the beam profiles in the various figures.

Multiple Firings Per Beam Line

According to the invention, multiple firings of a 1.5-D array 20 are implemented to obtain raw data for a given beam line $42_i$. For each firing associated with a given beam line the xz image plane 48 is the same. According to one aspect of this invention, the elevation aperture size 62 is changed for as many as all of the multiple firings. The elevation focus and apodization, being symmetrical, are unchanged, other than due to the impact of changing the elevation aperture. Because, elevation aperture effects elevation focus, elevation focus changes for each firing. There is no steering along the elevation for the 1.5-D array 20.

Figure 6:
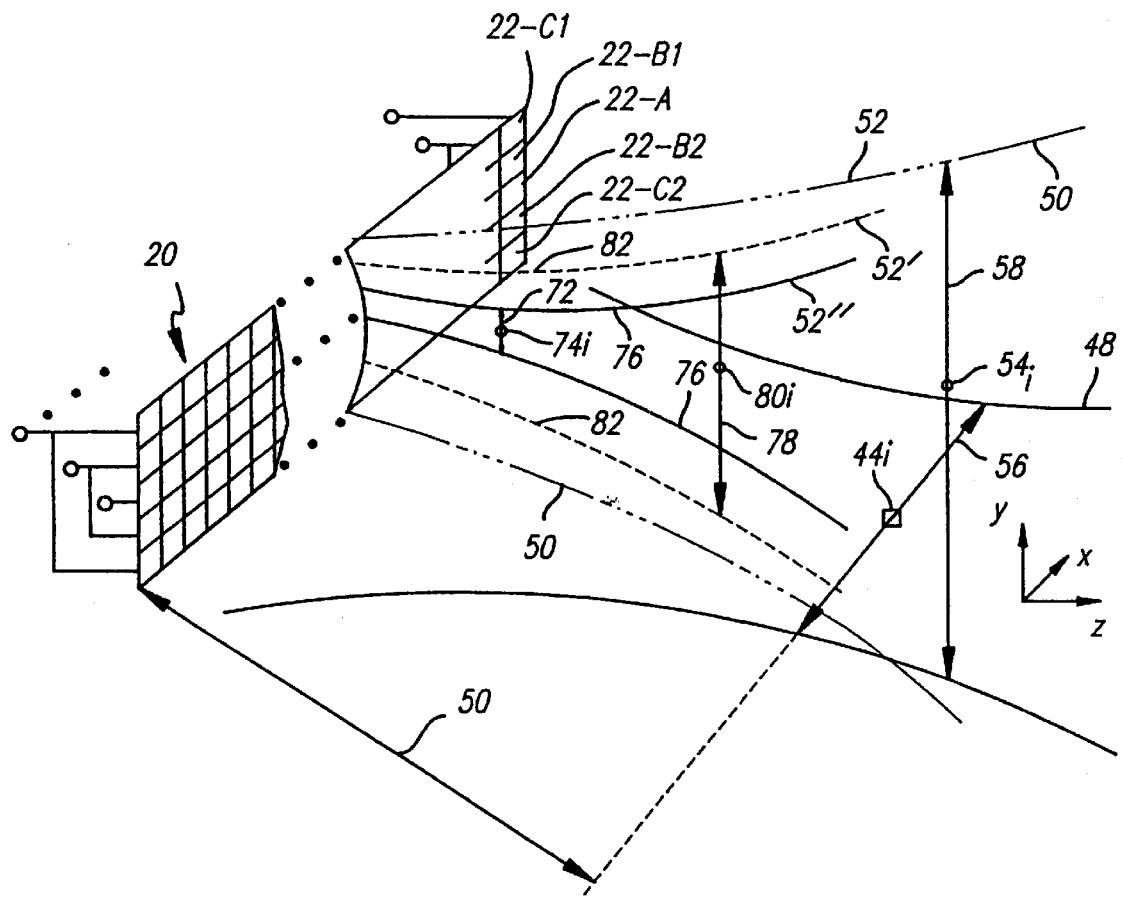
FIG. 6 is a diagram of a 1.5-D ultrasound transducer implementing a static scanhead switching method to obtain a given beam line from multiple array firings according to an embodiment of this invention.

FIG. 6 shows the unchanged xz image plane 48 and multiple yz elevation slices 52, 52' and 52" for an embodiment in which three firings are used to obtain a given beam line $42_i$. During one firing, the elevation aperture encompasses only the center row 22-A. The resulting yz elevation slice 52" has a width 72 and an elevation focus $74_i$. The −6 dB lines 76 for yz elevation slice 52" are shown as solid lines. During another firing, the elevation aperture encompasses the center row 22-A and the rows 22-B1, 22-B2 on each side of the center row. The resulting yz elevation slice 52' has a width 78 and an elevation focus $80_i$. The −6 dB lines 82 for yz elevation slice 52' are shown as dashed lines. During the remaining firing, the elevation aperture encompasses all five rows 22-A, 22-B1, 22-B2, 22-C1 and 22-C2. The resulting yz elevation slice 52 has a width 58 and an elevation focus $54_i$. The −6 dB lines 51 for yz elevation slice 52 are shown as dash-dot lines. The order of the firings may vary.

Figure 7:
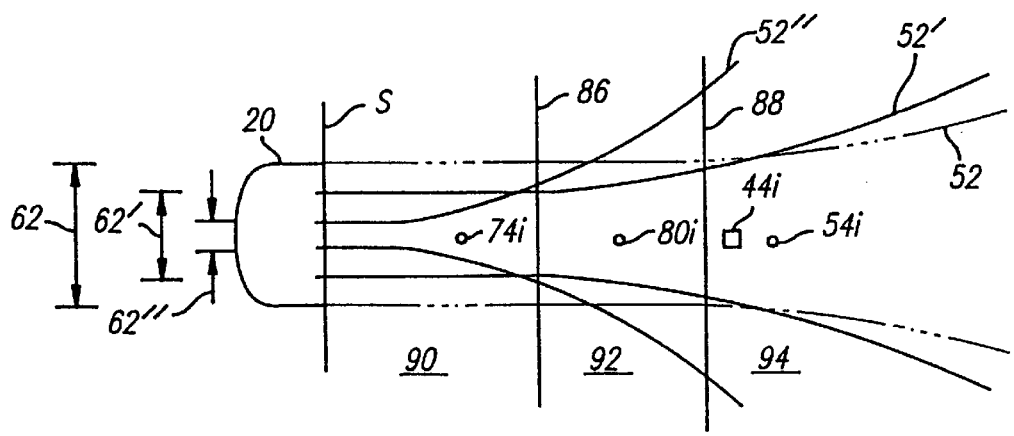
FIG. 7 is a diagram of the elevation slices for the multiple firings shown in FIG. 6.

FIG. 7 shows the 2-dimensional yz elevation slices 52, 52' and 52" of FIG. 6, along with the corresponding elevation aperture sizes 62, 62' and 62". Although the number of firings depicted is three, such number may vary. The minimum number of firings per beam line is one. The maximum number of firings per beam line is the number of elevation aperture permutations. For the 5 row embodiment illustrated, there are 3 possible elevation apertures (i.e., 3 permutations). The actual number of firings per beam line depends on the xz image plane focus 44 depth 50 and the desired frame rate.

Selecting Data From Each Firing to Obtain Beam Line Data

Referring to FIG. 7, in an embodiment having three elevation aperture permutations 62, 62' and 62", two break point depths 86, 88 are defined for processing received echo data. For a target depth beyond the deeper break point 88, three firings are performed per beam line 42. For a target depth between the first and second break points 86, 88 two firings are performed per beam line 42. For a target depth between the skin line S and the first break point 86, only one firing is performed per beam line 42. The target depth corresponds to the image plane focus depth 50 (see FIGS. 4–6).

Figure 8:
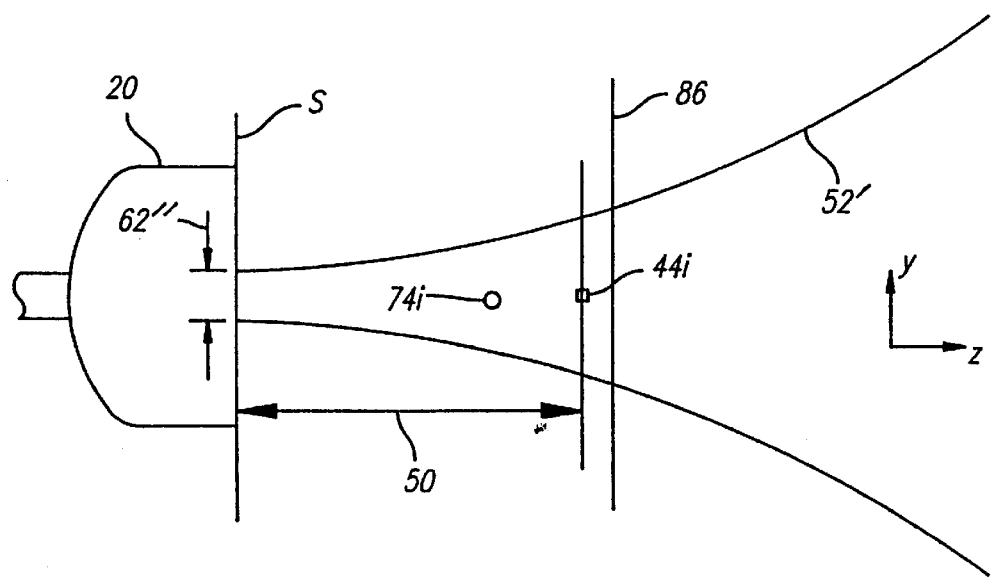
FIG. 8 is a diagram of an elevation slice for a step in which a single firing is used to obtain a beam line.

Consider first, the case where the target depth is less than the first break point depth 86. A given beam line $42_i$ within field of view 40 is obtained by performing a single firing using elevation aperture 62". The azimuth beamforming parameters are determined according to the given one of the beam lines 42 to be obtained. The result is an xz image plane similar to image plane 48 of FIG. 4 and a yz elevation slice 52" as shown in FIG. 8. The image plane focus 44 and focus depth 50 occur between the skin line S and the break point 86. The elevation focus is at focus 74.

Figure 9:
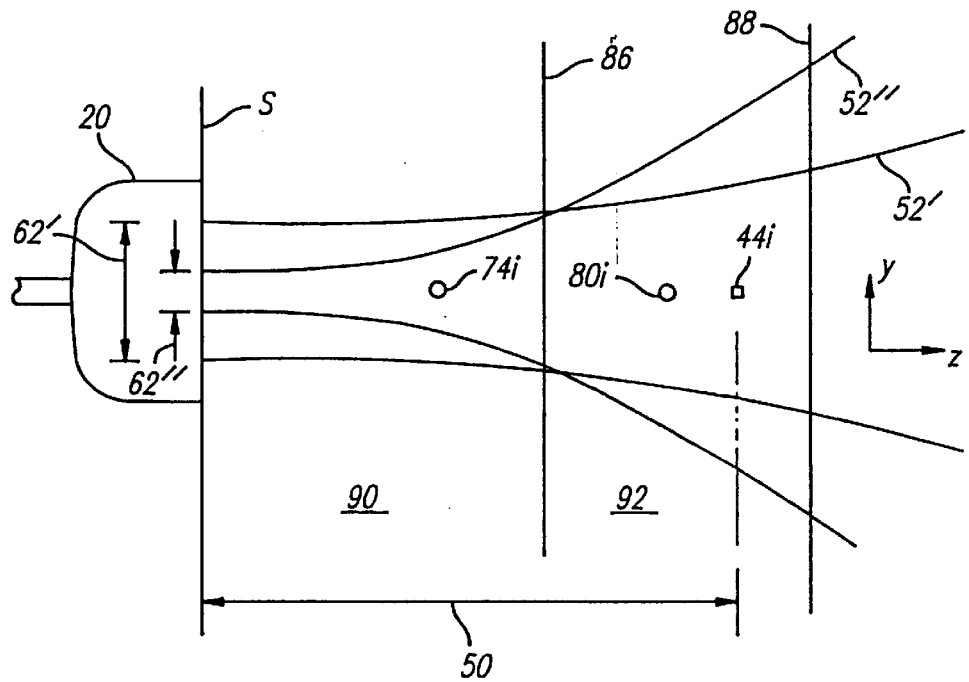
FIG. 9 is a diagram of an elevation slice for a case in which a two firings are used to obtain a beam line.

Consider next, the case where the target depth is between the first break point depth 86 and the second break point depth 88. A given beam line $42_i$ within field of view 40 is obtained by performing two firings per beam line 42. During a first firing the elevation aperture size 62" is used. During the second firing the elevation aperture size 62' is used. The order of the firings may vary. The azimuth beamforming parameters are determined according to the given one beam line to be obtained and are the same for both firings. The result is an image plane similar to the image plane 48 of FIG. 4 for each firing. FIG. 9 shows the yz elevation slice 52" for the first firing and the yz elevation slice 52' for the second firing. The image plane focus 44 and focus depth 50 occur between the first and second break point depths 86, 88 and remain the same for each firing. The elevation focus is at focus 74 during the first firing and at focus 80 during the second firing. To obtain the beam line $42_i$ the echo data corresponding to yz elevation slice 52" is used in region 90, and the echo data corresponding to yz elevation slice 52' is used in region 92. Thus, the echo data corresponding to region 92 is disregarded for the first firing having aperture size 62", and the echo data corresponding to region 90 is disregarded for the second firing having aperture size 62'.

Consider finally, the case where the target depth is beyond the second break point depth 88. A given beam line $42_i$ within field of view 40 is obtained by performing three firings per beam line 42. During a first firing the elevation aperture size 62" is used. During the second firing the elevation aperture size 62' is used. During the third firing the elevation aperture size 62 is used. The order of the firings may vary. The azimuth beamforming parameters again are determined according to the given one beam line to be obtained and are the same for each of the three firings. For each firing the result is an image plane similar to the image plane 48 of FIG. 4. FIG. 7 shows the yz elevation slice 52" for the first firing, the yz elevation slice 52' for the second firing, and the yz elevation slice 52 for the third firing. The image plane focus 44 and focus depth 50 occur beyond the second break point depth 88 and remain the same for each firing. The elevation focus is at focus 74 for the first firing, at focus 80 for the second firing, and at focus 54 for the third firing. To obtain the beam line $42_i$ the echo data corresponding to yz elevation slice 52" is used in region 90, the echo data corresponding to yz elevation slice 52' is used in region 92, and the echo data corresponding to yz elevation slice 52 is used in region 94. Thus, the echo data corresponding to regions 92, 94 are disregarded for the first firing having aperture 62". The echo data corresponding to regions 90, 94 are disregarded for the second firing having aperture 62'. The echo data corresponding to regions 90, 92 are disregarded for the third firing having aperture 62.

Note that the described methods are used for 1.5-D static scanhead arrays (or 2-D arrays programmed to function as a 1.5-D static scanhead array). By static it is meant that the elevation beamforming aperture does not change dynamically during a single firing/echo response. This is in contrast to a dynamic switching scheme in which the elevation aperture may vary with time to change the focus for a given firing as a function of time.

Blending Echo Data Near Region Boundaries

As described above, a beam line is formed by taking echo data from one region of one firing and echo data from another region for another firing. To avoid sudden changes in data at a boundary separating two such regions, however, it is preferred to blend the echo data from the two firings near the boundary between regions. Consider the beam profiles 52', 52" in FIG. 9. Echo data in region 90 from a first firing is combined with echo data from region 92 of a second firing to form the beam line. The boundary is the break point depth 86. Near the boundary within region 90, echo data from the second firing is blended with echo data from the first firing. Similarly in region 92 near the boundary, echo data from the first firing is blended with echo data from the second firing.

According to one embodiment blending is performed by applying a weight to the echo data from the respective firings. Within region 90 as the depth approaches break point 86 the weight of echo data from the first firing decreases toward 0.5 and that from the second firing increases toward 0.5. Then as the boundary is crossed into region 92 and the depth continues to increase, the weight of echo data from the first firing continues to decrease below 0.5 and that from the second firing continues to increase above 0.5. At some distance on each side of the boundary, echo data from only one firing is used. Thus, there is a window of depth range about a break point where echo data is weighted and blended to define echo data for the beam line. Outside such window within a given region echo data from only a corresponding firing defines the beam line echo data, while echo data from other firings is disregarded.

Alternative Embodiment

Figure 10:
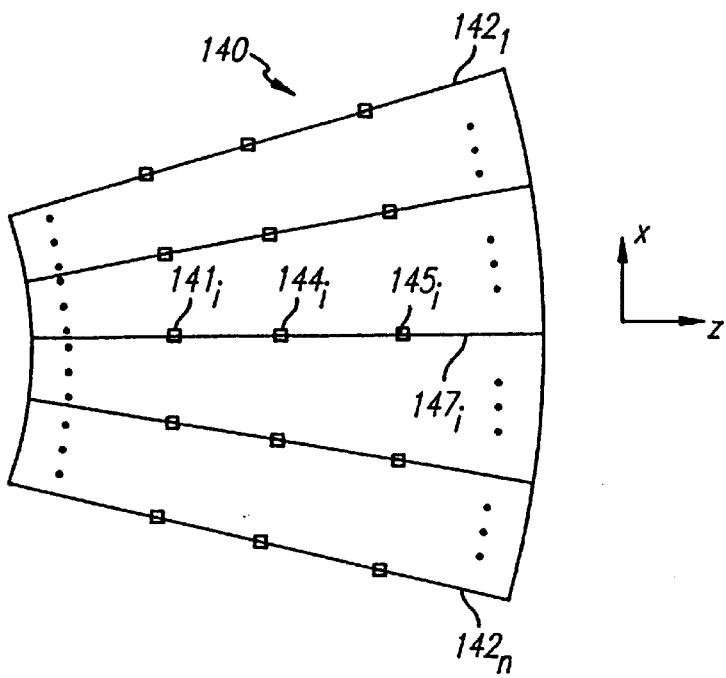
FIG. 10 is a diagram of a 1.5-D ultrasound transducer field of view formed by multiple beam lines having multiple foci per beam line.

In the embodiments described above, the single azimuth image plane focus remains the same for each firing associated with a given scan line $42_i$. According to an alternative embodiment the azimuth beamforming parameters are changed during each of the firings associated with a given beam line so as to vary the image plane focus during each firing. FIG. 10 shows a field of view 140 for a 1.5-D static scanhead transducer array 20 in which multiple foci are targeted per beam line 142. For example, for the beam line embodiment shown, each beam line $142_i$ corresponds to a transmitted beam having three foci $141_i$, $144_i$, $145_i$. In other embodiments fewer or more foci are used. For each image plane focus 141, 144, 145 of a given beam line 142 there is a separate firing of array 20. According to an aspect of this invention, the elevation aperture also is changed between one or more of such firings.

Figure 11:
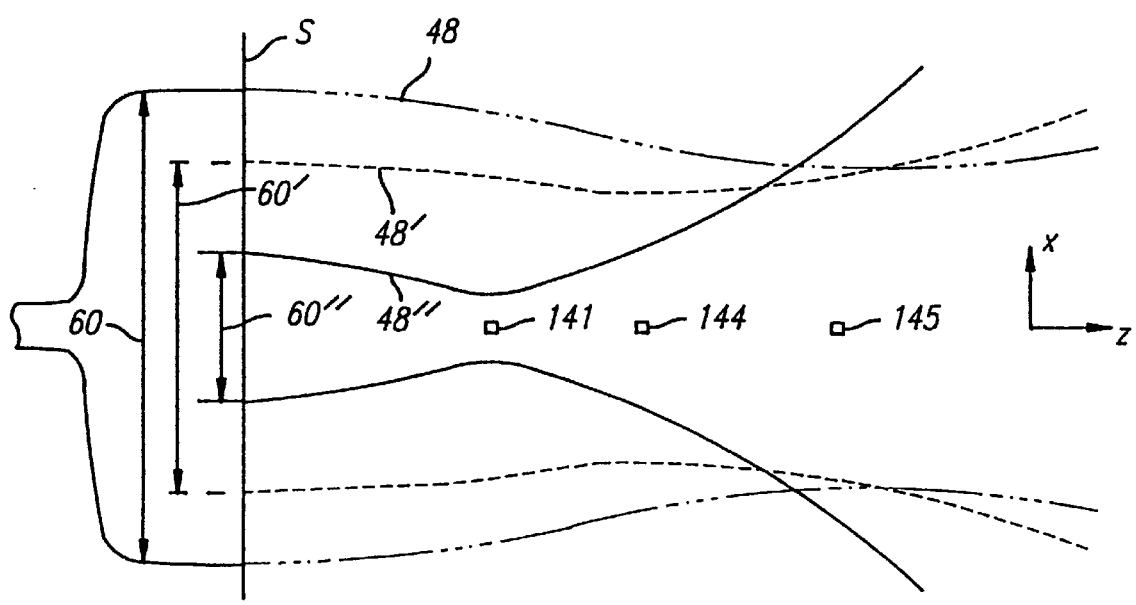
FIG. 11 is a diagram of an xz image plane for a given beam line of FIG. 10.

FIG. 11 shows the xz image planes 48, 48', 48" for the multiple firings. During a first firing the azimuth aperture size is length 60" resulting in an image plane 48" and a focus 141. During a second firing the azimuth aperture size is length 60' resulting in an image plane 48' and a focus 144. During the third firing the azimuth aperture size is length 60 resulting in an image plane 48 and a focus 145. The order of firings may vary.

Figure 12:
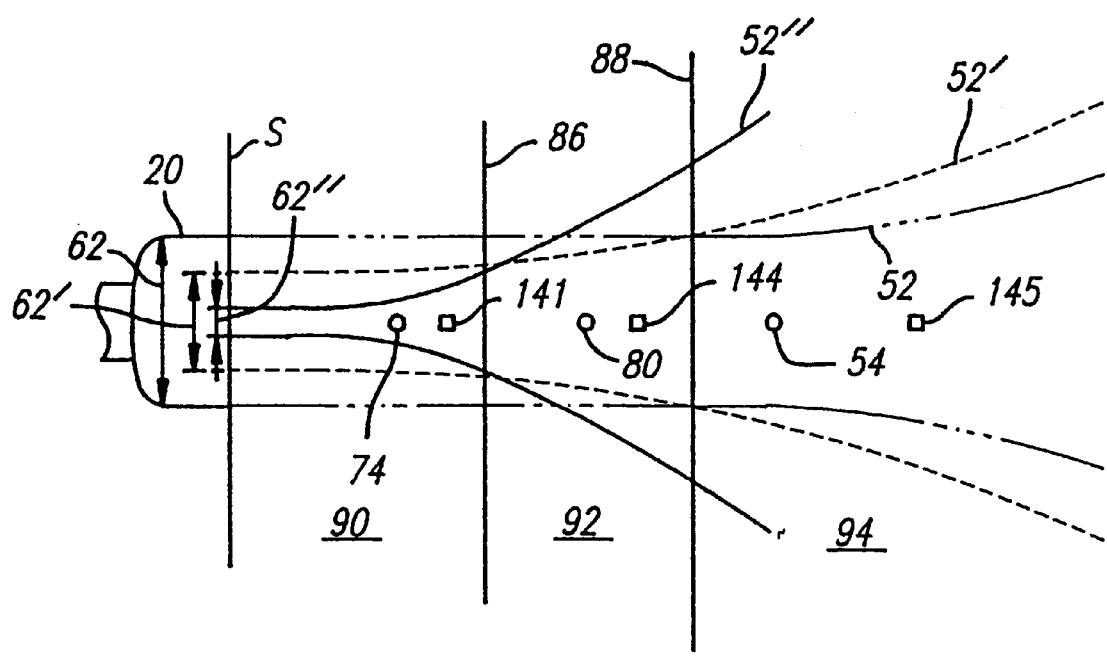
FIG. 12 is a diagram of a yz elevation slice for a given beam line of FIG. 11 for a 1.5-D ultrasound transducer implementing a static scanhead switching method according to an embodiment of this invention.

FIG. 12 shows the yz elevation slices 52, 52' and 52" for the multiple firings. For the first firing the image plane focus 141 is between the skin line S and the first break point 86. Elevation aperture size 62" is used for such firing. For the second firing the image plane focus 144 is between the first and second break points 86, 88. Elevation aperture size 62' is used for such firing.

For the third firing the image plane focus 145 is beyond second break point 88. Elevation aperture size 62 is used for such firing. To obtain the beam line 142$_i$ the echo data corresponding to yz elevation slice 52" is used in region 90, the echo data corresponding to yz elevation slice 52' is used in region 92, and the echo data corresponding to yz elevation slice 52 is used in region 94. Thus, the echo data corresponding to regions 92, 94 are disregarded for the first firing having aperture 62". The echo data corresponding to regions 90, 94 are disregarded for the second firing having aperture 62'. The echo data corresponding to regions 90, 92 are disregarded for the third firing having aperture 62. Alternatively, the echo data is blended near the region boundaries as described above.

For an embodiment in which multiple foci within the image plane are used, multiple firings are performed per beam line. Following is the logic for determining what length elevation aperture to use for each firing.

```
IF image plane focus for current firing is less than first break point
    THEN use narrowest elevation aperture size
ELSE IF image plane focus for current firing is between first and
        second break point
    Then use second narrowest elevation aperture size
ELSE IF image plane focus for current firing is second and third
        break point
    Then use third narrowest elevation aperture size
:
ENDIF
```

The logic continues depending on the number of break points implemented. As described above the number of break points equals the number of elevation aperture permutations minus one. Thus, for the 3 elevation aperture permutations of array 20, there are two break points. The third contingency in the above logic (e.g., second ELSE IF clause) thus becomes, "ELSE IF image plane focus for current firing is beyond the second break point."

By limiting the scanhead switching to change the elevation aperture no more than once per firing, a lower frame rate is used to obtain beam lines across the entire field of view 40 as compared to dynamic switching schemes (e.g., dynamic elevation aperture switching). Such penalty, however, is not incurred for embodiments where multiple foci are targeted per beam line, (e.g., where the azimuth beamforming parameters are changed with each firing).

For another alternative embodiment in which there are a multiple number image plane foci per beam line, but such number is less than the number of elevation aperture permutations similar elevation aperture switching schemes are used. In one method there are as many firings per beam line as there are image plane foci per beam line. The elevation aperture size for a given firing is based upon the depth of the image plane foci relative to the breakpoint depths. This is the same decision criteria as for the multiple image foci embodiment described above. In another method there are as many firings per beam line as there are elevation aperture permutations. A different elevation aperture size is used for each firing. One of the multiple image plane foci is used per firing, wherein all the image plane foci are eventually used for each beam line. Thus, the same image plane focus is used on more than one firing per beam line.

Exemplary Host Medical Diagnostic Ultrasound System

FIG. 13 shows an ultrasound medical diagnostic imaging system 210. The system 210 emits ultrasound signals and detects response echoes to scan a target area within a patient's anatomy. The ultrasound system 210 includes a system controller 212, transmitter 214, transducer 20, receiver 218, vector processing subsystem(s) 222, Doppler processing subsystem 223, image processing subsystem 224, scan converter 226 and display 228. The system controller 212 provides a user interface 230 (e.g., control panel, display menu, keyboard) and controls system operations. In operation, the system controller 212 triggers the transmitter 214 to generate electrical signals for output to the transducer 20. The transducer 20 converts the electrical signals into an ultrasound transmit wave-pattern. Typically, the transducer 20 is positioned adjacent to and in contact with a patient's anatomy. The transmit wave-pattern propagates into the patient's anatomy where it is refracted, absorbed, dispersed and reflected. The degree of refraction, absorption, dispersion and reflection depends on the uniformity, density and structure of the encountered anatomy. Of interest is the reflected or backscattered components which propagate back to the transducer 20. These echoes are sensed by the transducer 20 and converted back into electrical signals. The electrical signals are input to a receiver 218 which amplifies the signals. A beamformer portion of receiver 218 groups the echo signals into correlated frames of data scans for given target areas.

After beamforming, raw beamformed data is fed to back-end processing subsystems 222–226. The back-end processing subsystems typically perform echo processing, Doppler processing, color flow processing, image processing, scan conversion and video processing. Conventional image processing of raw beamformed echo data includes generating gray-scale image data corresponding to a patient's target area. Typically, raw data is encoded by applying a gray-scale value proportional to the echo intensity for a given vector sample. Scan conversion is performed to fill in values for pixels between vector samples. For some applications the encoded image data also is electronically stored in a memory medium, such as a permanent memory storage device (e.g., disk or tape) or a temporary storage device (e.g., solid state memory). Also, the encoded image data often is printed out in a hard copy format, such as a photograph.

What is claimed is:

1. A method for generating a beam line within a field of view of an ultrasound 1.5-D transducer array for a given scanning cycle, comprising the steps of:

defining a break point depth;

for an image plane focus shallower than the break point depth, generating the beam line for the given scanning cycle by firing the transducer array once, wherein elevation aperture is of a first size for the firing; and for an image plane focus deeper than the break point depth, performing multiple firings of the transducer array to generate the beam line for the given scanning cycle, wherein elevation aperture is of a first size during one of the multiple firings and is of a second size during another of the multiple firings, the second size being greater than the first size; wherein receive beamforming parameters along the azimuth of the array are the same for receiving echo data in response to the multiple firings, and wherein elevation aperture comprises at least one row of transducer elements within the 1.5-D array for the first size and comprises at least three rows of transducer elements within the 1.5-D array for the second size.

2. The method of claim 1, in which image plane focus is the same for each firing and the beam line has only one image plane focus.

3. The method of claim 1, in which a first region comprises depth shallower than the break point, and at least one other region comprises depth deeper than the break point, and wherein echo data within the first region associated with the beam line for the given scan cycle comprises echo data within the first region for said one firing, wherein echo data in the first region outside a window about the break point and associated with the beam line for the given scan cycle excludes echo data from said another of the multiple firings, and wherein echo data within the at least one other region outside the window about the break point and associated with the beam line for the given scan cycle excludes echo data from said one firing.

4. The method of claim 1, in which a first region comprises depth shallower than the break point, and at least one other region comprises depth deeper than the break point, and wherein echo data associated with the beam line for the given scan cycle comprises echo data within the first region for said one firing, and wherein echo data outside the first region is disregarded for said one firing, and echo data within the first region is disregarded for said another firing.

5. The method of claim 1, in which the break point depth is a first break point depth and further comprising the step of defining a second break point depth, and
    wherein for an image plane focus between the first break point depth and second break point depth, performing two firings of the transducer array to generate the beam line, wherein elevation aperture is of the first size during one of the two firings and is of the second size during the other of the two firings, the second size being greater than the first size; and
    wherein for an image plane focus deeper than the second break point depth, performing three firings of the transducer array to generate the beam line, wherein elevation aperture is of the first size during one of the three firings, is of the second size during another of the three firings, and is of a third size during yet another of the three firings, the third size being greater than the second size and the second size being greater than the first size.

6. The method of claim 5, in which a first region comprises depth shallower than the first break point, a second region comprises depth between the first and second break point, and a third region comprises depth deeper than the second break point, and wherein echo data associated with the beam line for the given scan cycle comprises echo data within the first region for each firing having an elevation aperture of the first size, echo data within the second region for each firing having an elevation aperture of the second size, and echo data within the third region for each firing having an elevation aperture of the third size, and wherein echo data within the second region and third region is disregarded for each said firing having an elevation aperture of the first size, echo data within the first region and third region is disregarded for each said firing having an elevation aperture of the second size, and echo data within the first region and second region is disregarded for each said firing having an elevation aperture of the third size.

7. The method of claim 5, in which a first region comprises depth shallower than the first break point, a second region comprises depth between the first and second break point, and a third region comprises depth deeper than the second break point, and wherein echo data associated with the beam line for the given scan cycle comprises echo data within the first region for each firing having an elevation aperture of the first size, echo data within the second region for each firing having an elevation aperture of the second size, and echo data within the third region for each firing having an elevation aperture of the third size, and wherein echo data from each said firing having an elevation aperture of the first size and each said firing having an elevation aperture of the second size are blended for echo data in the first region within a first window of depth about the first break point, and wherein echo data from each firing having an elevation aperture which is not of the first size is disregarded for echo data in the first region outside the first window.

8. A method for generating a beam line having multiple image plane foci within a field of view of an ultrasound 1.5-D transducer array for a given scanning cycle, comprising the steps of:
    defining a break point depth;
    performing a number of firings of the transducer array for each beam line generated for a given scanning cycle, wherein there is at least one firing per image plane focus along said beam line, each firing having an image plane focus at only one of the multiple image plane foci;
    wherein for each firing associated with the beam line being generated for the given scanning cycle, elevation aperture is set to a first aperture size for image plane focus which is shallower than the break point depth and is set to another aperture size, greater than the first aperture size, for image plane focus which is deeper than the break point depth; and
    wherein elevation beamforming parameters are fixed during a given firing and a corresponding receive time period responsive to said given firing, and wherein elevation aperture comprises at least one row of transducer elements within the 1.5-D array for the first aperture size and comprises at least three rows of transducer elements within the 1.5-D array for another aperture size.

9. The method of claim 8, in which a first region comprises depth shallower than the break point, and at least one other region comprises depth deeper than the break point, and wherein echo data associated with the beam line for the given scan cycle comprises echo data within the first region for each firing in which elevation aperture is set to the first aperture size, and wherein echo data in the first region outside a window about the break point and associated with the beam line for the given scan cycle excludes echo data from each firing in which elevation aperture is not set to the first aperture size.

10. The method of claim 8, in which a first region comprises depth shallower than the break point, and at least one other region comprises depth deeper than the break point, and wherein echo data associated with the beam line for the given scan cycle comprises echo data within the first region for each firing in which elevation aperture is set to the first aperture size, and wherein echo data within the first region is disregarded for each firing in which elevation aperture is not set to the first aperture size.

11. The method of claim 8, in which a beam line has at least three image plane foci, and in which the break point depth is a first break point depth and further comprising the step of defining a second break point depth, and wherein for each firing associated with the beam line being generated for the given scanning cycle, elevation aperture is set to a second aperture size for image plane focus which is between the first break point depth and second break point depth and is set to a third aperture size for image plane focus which is deeper than the second break point depth, the third aperture size greater than the second aperture size, the second aperture size greater than the first aperture size.

12. The method of claim 11, in which a first region comprises depth shallower than the first break point, a second region comprises depth between the first and second break point, and at least one third region comprises depth deeper than the second break point, and wherein echo data associated with the beam line for the given scan cycle comprises echo data within the first region for each firing having elevation aperture set to the first aperture size, echo data within the second region for each firing having elevation aperture set to the second aperture size, and echo data within at least one of said at least one third regions for each firing having elevation aperture set to the third aperture size, and wherein echo data from each said firing having an elevation aperture of the first size and each said firing having an elevation aperture of the second size are blended for echo data in the first region within a first window of depth about the first break point, and wherein echo data from each firing having an elevation aperture which is not of the first size is disregarded for echo data in the first region outside the first window.

13. The method of claim 11, in which a first region comprises depth shallower than the first break point, a second region comprises depth between the first and second break point, and at least one third region comprises depth deeper than the second break point, and wherein echo data associated with the beam line for the given scan cycle comprises echo data within the first region for each firing having elevation aperture set to the first aperture size, echo data within the second region for each firing having elevation aperture set to the second aperture size, and echo data within at least one of said at least one third regions for each firing having elevation aperture set to the third aperture size, and wherein echo data within the second region and each of said at least one third regions is disregarded for each firing having elevation aperture set to the first aperture size, wherein echo data within the first region and each of said at least one third regions is disregarded for each firing having elevation aperture set to the second aperture size, and wherein echo data within the first region and second region is disregarded for each firing having elevation aperture set to the third aperture size.

14. A medical diagnostic ultrasound system for generating a beam line within a field of view of an ultrasound transducer array for a given scanning cycle, comprising:

a 1.5-D ultrasound transducer array comprising a plurality of rows of transducer elements, each row comprising a plurality of transducer elements, the plurality of rows being symmetrically arranged along elevation, in which each given transducer element in one row is electrically coupled to a corresponding transducer elements in a row symmetrical to said one row;

a transmitter electrically coupled to the array for generating electrical signals at the array causing the array in response to perform a firing in which ultrasound energy is emitted from the array;

a receiver electrically coupled to the array for receiving electrical signals from the array, the received electrical signals corresponding to ultrasound energy echoed back to the array converted into electrical echo signals;

a beamformer coupled to the array for defining beamforming transmit and receive parameters for the array;

means for defining a break point depth;

for an image plane focus shallower than the break point depth, means for generating a beam line within a field of view of the transducer array for a given scanning cycle by firing the transducer array once, wherein elevation aperture is of a first size for the firing; and for an image plane focus deeper than the break point depth, means for performing multiple firings of the transducer array to generate the beam line for the given scanning cycle, wherein elevation aperture is of a first size during one of the multiple firings and is of a second size during another of the multiple firings, the second size being greater than the first size.

15. The system of claim 14, in which image plane focus is the same for each firing and the beam line has only one image plane focus.

16. The system of claim 14, in which a first region comprises depth shallower than the break point, and at least one other region comprises depth deeper than the break point, and wherein echo data within the first region associated with the beam line for the given scan cycle comprises echo data within the first region for said one firing, wherein echo data in the first region outside a window about the break point and associated with the beam line for the given scan cycle excludes echo data from said another of the multiple firings, and wherein echo data within the at least one other region outside the window about the break point and associated with the beam line for the given scan cycle excludes echo data from said one firing.

17. The system of claim 14, in which a first region comprises depth shallower than the break point, and at least one other region comprises depth deeper than the break point, and wherein echo data associated with the beam line for the given scan cycle comprises echo data within the first region for said one firing, and wherein echo data outside the first region is disregarded for said one firing and echo data within the first region is disregarded for said another firing.

18. The system of claim 14, in which the break point depth is a first break point depth and further comprising means for defining a second break point depth, and wherein for an image plane focus between the first break point depth and second break point depth, the performing means performs two firings of the transducer array to generate the beam line, wherein elevation aperture is of the first size during one of the two firings and is of the second size during the other of the two firings, the second size being greater than the first size; and wherein for an image plane focus deeper than the second break point depth, the performing means performs three firings of the transducer array to generate the beam line, wherein elevation aperture is of the first size during one of the three firings, is of the second size during another of the three firings, and is of a third size during yet another of the three firings, the third size being greater than the second size and the second size being greater than the first size.

19. A medical diagnostic ultrasound system for generating a beam line having multiple image plane foci within a field of view of an ultrasound transducer array for a given scanning cycle, comprising:
- a 1.5-D ultrasound transducer array comprising a plurality of rows of transducer elements, each row comprising a plurality of transducer elements, the plurality of rows being symmetrically arranged along elevation, in which each given transducer element in one row is electrically coupled to a corresponding transducer elements in a row symmetrical to said one row;
- a transmitter electrically coupled to the array for generating electrical signals at the array causing the array in response to perform a firing in which ultrasound energy is emitted from the array;
- a receiver electrically coupled to the array for receiving electrical signals from the array, the received electrical signals corresponding to ultrasound energy echoed back to the array converted into electrical echo signals;
- a beamformer coupled to the array for defining beamforming transmit and receive parameters for the array;
- means for defining a break point depth;
- means for performing a number of firings of the transducer array for each beam line generated for a given scanning cycle, wherein there is at least one firing per image plane focus along said beam line, each firing having an image plane focus at only one of the multiple image plane foci;
- wherein for each firing associated with the beam line being generated for the given scanning cycle, elevation aperture is set to a first aperture size for image plane focus which is shallower than the break point depth and is set to another aperture size, greater than the first aperture size, for image plane focus which is deeper than the break point depth; and
- wherein elevation beamforming parameters are fixed during a given firing and a corresponding receive time period responsive to said given firing, and wherein elevation aperture comprises at least one row of transducer elements within the 1.5-D array for the first aperture size and comprises at least three rows of transducer elements within the 1.5-D array for another aperture size.

20. The system of claim 19, in which a first region comprises depth shallower than the break point, and at least one other region comprises depth deeper than the break point, and wherein echo data within the first region associated with the beam line for the given scan cycle comprises echo data within the first region for said one firing, wherein echo data in the first region outside a window about the break point and associated with the beam line for the given scan cycle excludes echo data from said another of the multiple firings, and wherein echo data within the at least one other region outside the window about the break point and associated with the beam line for the given scan cycle excludes echo data from said one firing.

21. The system of claim 19, in which a beam line has at least three image plane foci, and in which the break point depth is a first break point depth and further comprising means for defining a second break point depth, and
- wherein for each firing associated with the beam line being generated for the given scanning cycle, elevation aperture is set to a second aperture size for image plane focus which is between the first break point depth and second break point depth and is set to a third aperture size for image plane focus which is deeper than the second break point depth, the third aperture size greater than the second aperture size, the second aperture size greater than the first aperture size.

22. The system of claim 21, in which a first region comprises depth shallower than the first break point, a second region comprises depth between the first and second break point, and at least one third region comprises depth deeper than the second break point, and
- wherein echo data associated with the beam line for the given scan cycle comprises echo data within the first region for each firing having elevation aperture set to the first aperture size, echo data within the second region for each firing having elevation aperture set to the second aperture size, and echo data within at least one of said at least one third regions for each firing having elevation aperture set to the third aperture size, and
- wherein echo data from each said firing having an elevation aperture of the first size and each said firing having an elevation aperture of the second size are blended for echo data in the first region within a first window of depth about the first break point, and wherein echo data from each firing having an elevation aperture which is not of the first size is disregarded for echo data in the first region outside the first window.

* * * * *